United States Patent [19]

Mumme et al.

[11] Patent Number: 5,423,827
[45] Date of Patent: Jun. 13, 1995

[54] SURGICAL JIG FOR FEMORAL KNEE PROSTHESIS

[75] Inventors: Charles W. Mumme; Jeffery C. Higgins, both of Austin, Tex.

[73] Assignee: Intermedics Orthopedics, Inc., Austin, Tex.

[21] Appl. No.: 252,695

[22] Filed: Jun. 2, 1994

[51] Int. Cl.⁶ .............................................. A61B 17/00
[52] U.S. Cl. .................................... 606/96; 606/87; 606/79; 606/80; 408/115 R
[58] Field of Search ...................... 605/79, 80, 87, 88, 605/89, 96, 97, 98; 408/115 R, 97, 241 B

[56] References Cited

U.S. PATENT DOCUMENTS

| | | | |
|---|---|---|---|
| 4,667,664 | 5/1987 | Taylor et al. | 606/64 |
| 4,952,213 | 8/1990 | Bowman et al. | 606/88 |
| 5,282,803 | 2/1994 | Lackey | 606/96 |
| 5,364,402 | 11/1994 | Mumme et al. | 606/96 |

OTHER PUBLICATIONS

"Specialist Modified Femoral Drill Guide" Johnson & Johnson Orthopedics 1993.
Product Literature, Depuy 1993.

*Primary Examiner*—Stephen C. Pellegrino
*Assistant Examiner*—Scott B. Markow
*Attorney, Agent, or Firm*—John R. Merkling

[57] ABSTRACT

A surgical jig for orienting a femoral component of a prosthetic knee prosthesis angularly with respect to the axis of the patient's femur which jig utilizes a single drill plate or guide for condylar pins, but permits variation in the placement of those pins. The jig comprises a distal plate which is placed against the distal end of the femur. The distal plate has two condyle fingers for grasping the posterior side of the femoral condyles. Gage means are provided to measure the size of the distal end of the femur. A rotatable drill guide permits the surgeon to adjust the placement of two drill bores for receiving condyle pins on a femoral component of a knee prosthesis.

9 Claims, 4 Drawing Sheets

SURGICAL JIG FOR FEMORAL KNEE PROSTHESIS

FIELD OF OUR INVENTION

Our invention relates to apparatus for orthopedic surgery and particularly to jigs for implanting femoral components of knee prostheses.

BACKGROUND OF OUR INVENTION

Orthopedic prosthetic knees usually comprise a tibial component and a femoral component. In some instances, an artificial patella may also be provided. The tibial component frequently has a metal baseplate which is adapted to be mounted on a resected proximal end of the tibia. The baseplate has various fixation means to attach it to the tibia as, for example, a central shaft extending into the medullar canal, pins, porous or textured areas for bone ingrowth, or bone screws. On the base is mounted an articulating surface, usually made of ultra high molecular weight polyethylene. This articulating surface forms two condyle compartments: a larger medial compartment and a somewhat smaller lateral compartment.

The femoral compartment of the knee prosthesis is mounted on the resected distal end of the femur. The component is usually all metal and presents artificial condyles, one medial and one lateral, which slidingly engage the articulating surface of the tibial component. The femoral component is also affixed to its bone by various means, including a medullar shaft, porous or textured surfaces, or pins. In particular, pins are frequently provided located behind each condyle and extending in a direction which corresponds to the major axis of the femur. These pins help to establish rotational stability of the component with respect to the femur.

The effectiveness of a knee prosthesis is dependent, among other things, on the degree to which the two implanted components implanted correspond with the anatomy of the particular patient. As the leg of a patient moves, the components of the knee prosthesis can be expected to articulate against one another and their interaction will be effected by the accuracy of implantation with respect to the patient's bone. Jigs and other surgical apparatus assist surgeons in accurately placing the components of the prosthesis. Jigs for providing holes or starting bores for the condyle pegs described above are known. It is also known, however, that human anatomy varies from patient to patient. The optimum orientation of the components and in particular the femoral component varies within what is usually a small and well defined range. It is desirable to provide a jig which can accommodate such variation from patient to patient. Some jigs of this kind are available. For example, Richards Medical Products has marketed a femoral component jig for the condylar pins having separate drill hole plates for a range of angular variation. There remains, however, need for continued improvement in surgical apparatus.

SUMMARY OF OUR INVENTION

We have invented a surgical jig for orienting a femoral component of a prosthetic knee prosthesis angularly with respect to the axis of the patient's femur which jig utilizes a single drill plate or guide for condylar pins, but permits variation in the placement of those pins. The jig comprises a distal plate which is placed against the distal end of the femur. The distal plate has two condyle fingers for grasping the posterior side of the femoral condyles. Gage means are provided to measure the size of the distal end of the femur. A rotatable drill guide permits the surgeon to adjust the placement of two drill bores for receiving condyle pins on a femoral component of a knee prosthesis.

With the foregoing in mind, it is an object of our invention to provide a jig for aid in implanting a femoral component of a knee prosthesis, the jig having variable placement of condyle pins.

Another object of our invention is to provide such a jig wherein a single drill guide can be placed in selected positions to accommodate placement of the femoral component.

These and other objects and features of our invention will be apparent from the following detail description taken with reference to the accompanying drawings.

DETAILED DESCRIPTION OF OUR PREFERRED EMBODIMENT

Figure 1:
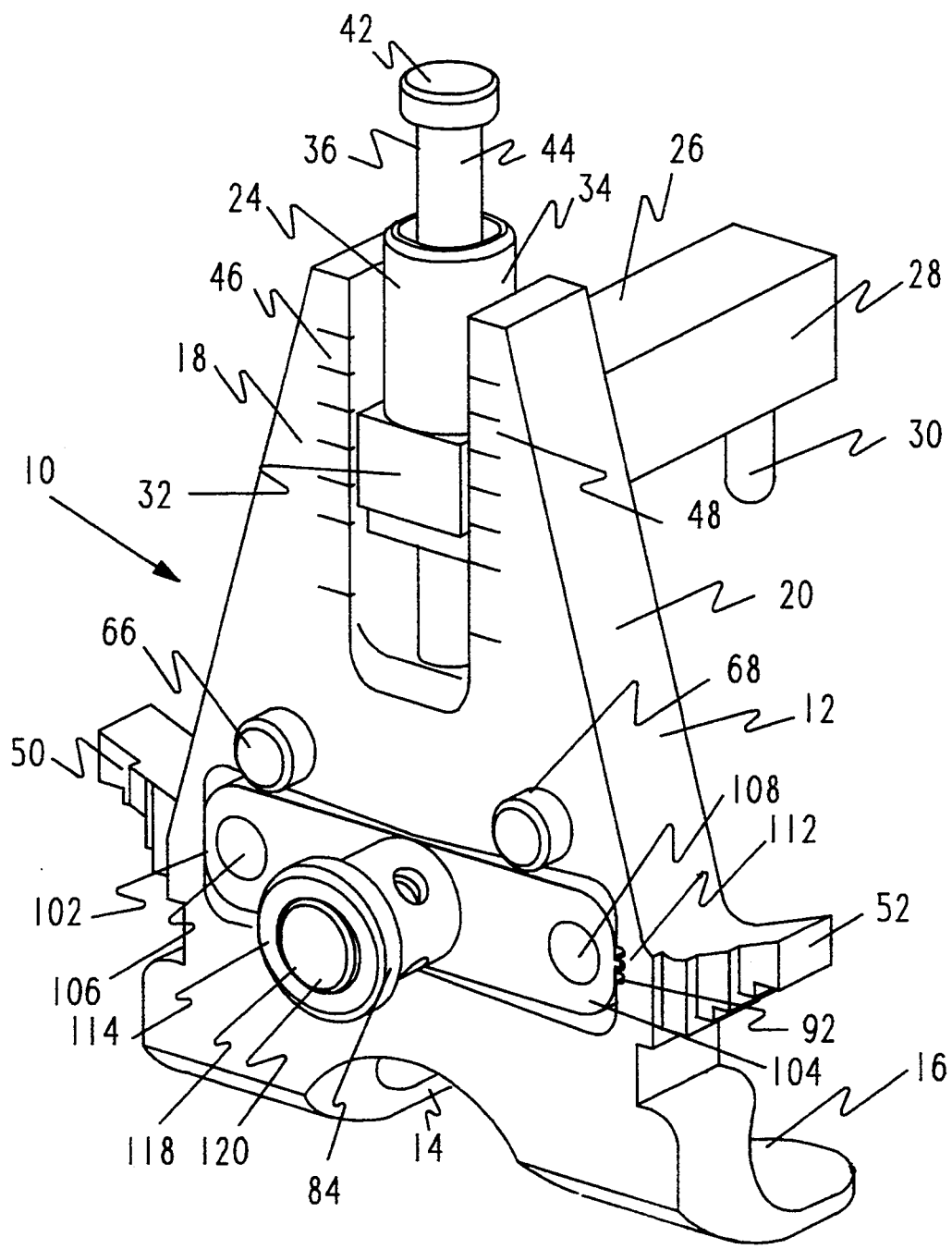
FIG. 1 is a prospective view of a jig for a femoral component of a knee prosthesis in accordance with our invention.
Figure 2:
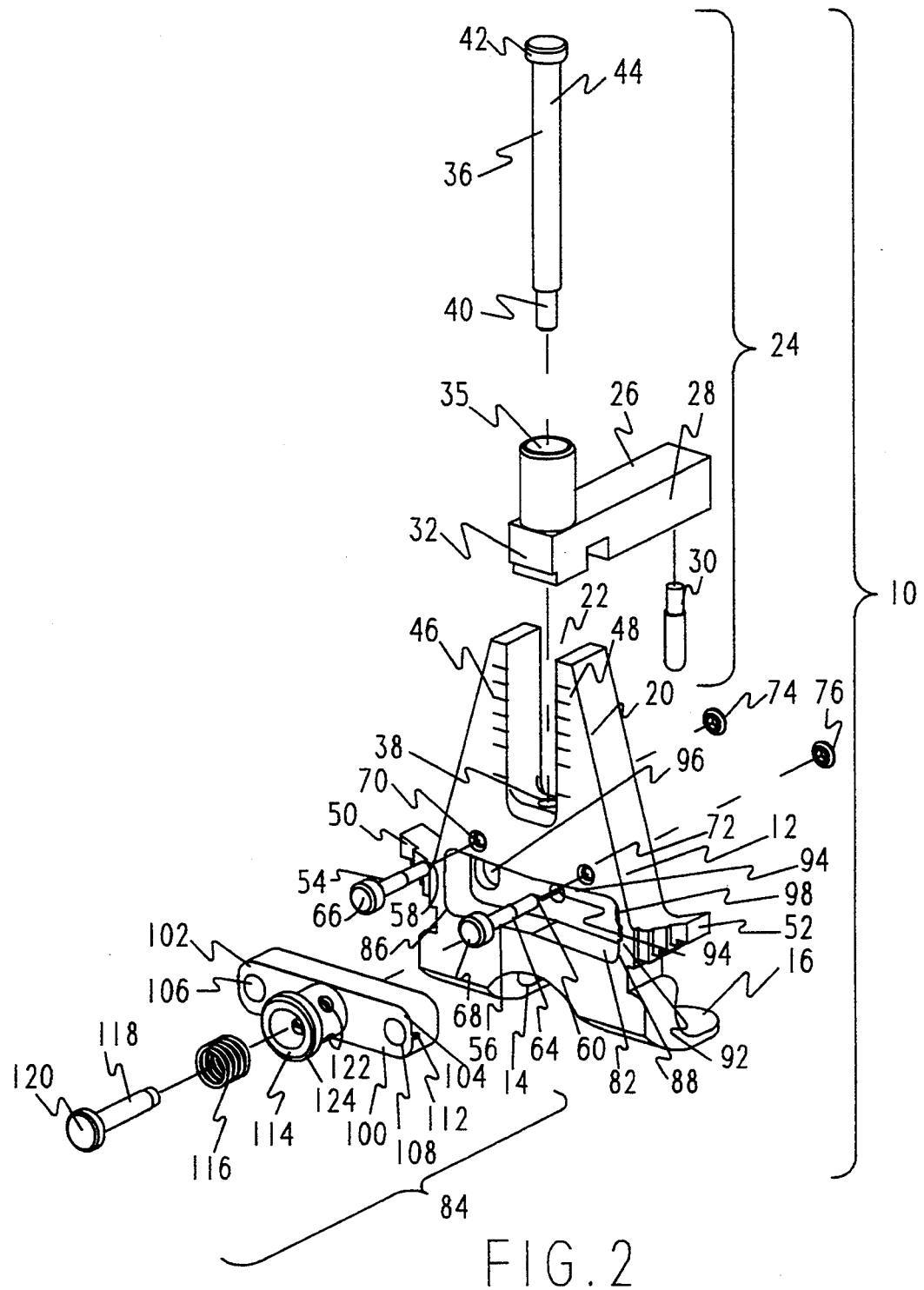
FIG. 2 is an exploded perspective view of the jig of FIG. 1.
Figure 3:
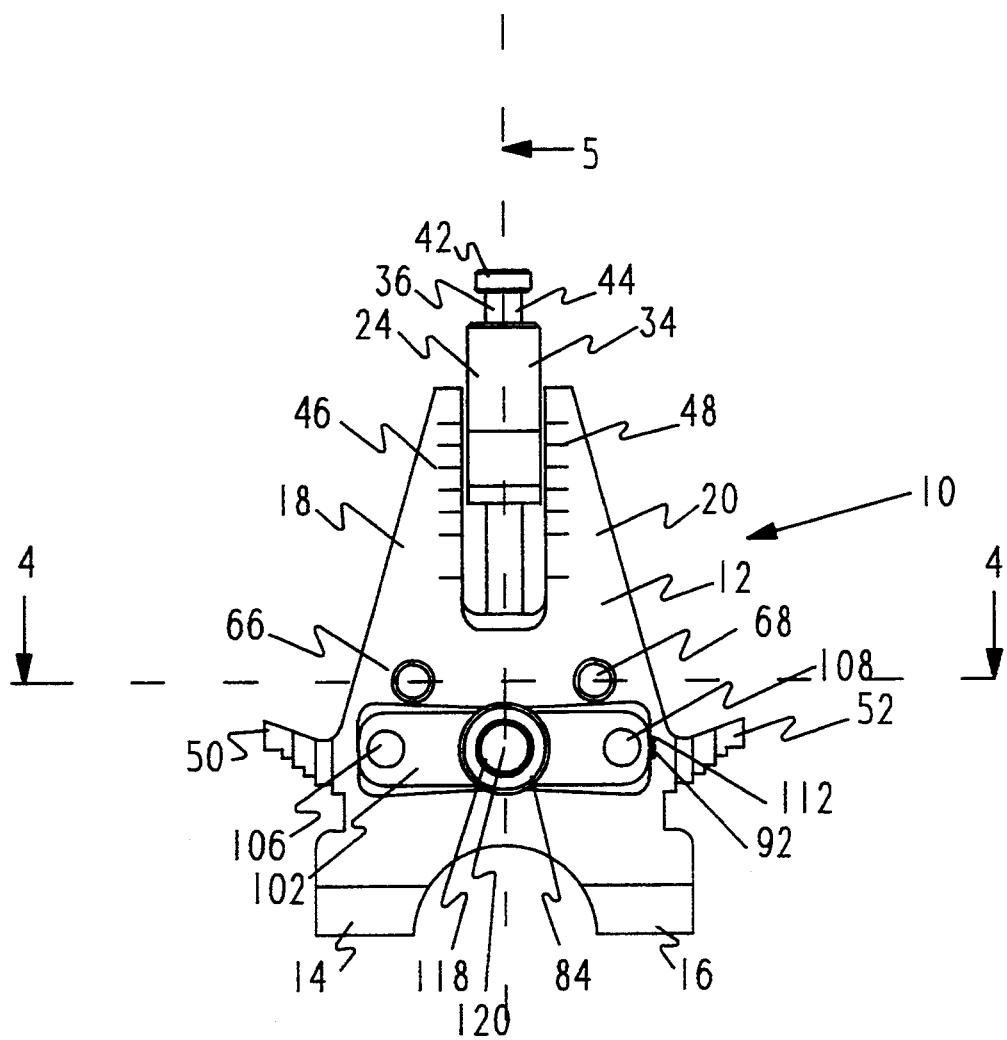
FIG. 3 is a front plan view of the jig of FIG. 1.

FIG. 1 illustrates a jig, generally designated 10, for implanting a femoral component of a knee prosthesis. In FIG. 2, the jig is illustrated in exploded perspective view. The jig 10 comprises a distal plate or base 12 which is adapted to be placed against the distal end of a femur. The plate 12 has two fingers 14, 16 which fit around a posterior side of the femoral condyles. Opposite the fingers 14, 16 there are two extensions, 18, 20 which define a slot 22. Gage means, generally designated 24, ride in the slot 22 for measuring the thickness of the individual patient's distal femur. The gage means 24 comprise an arm 26 which extends proximally from the plate 12. At one end 28 of the arm 26, spaced away from the plate 12, a feeler pin 30 is provided. This pin will be brought in contact with the patient's femur when a measurement is to be made. At a second end 32 of the arm 26 there is hollow cylindrical guide 34. A through bore extends through the guide 34 and the second end 32 of the arm 26. A rod 36 passes through the through bore 35 and is secured in a blind bore 38 in the body 12. The arm 26 can thus be displaced along the rod 36 when a measurement is to be made. A first end 40 of the rod 36 is threaded into the bore 38 or press fit therein or secured by some other conventional means. A head 42 at a second end 44 of the rod 36 prevents the arm 26 from being removed. Scales 46, 48 on the extensions 18 and 20 adjacent the slot 22 allow the thickness of the femur to be determined directly.

On either side of the plate 12, width gages 50, 52 allow the surgeon to determine the width of the distal end of the femur. Knowing the thickness of the femur and its width, the surgeon can better select an appropriate size of femoral component.

Figure 4:
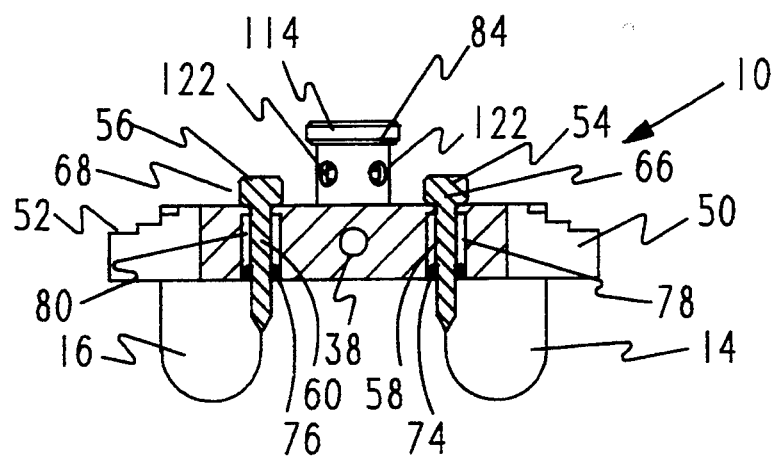
FIG. 4 is a through section of the jig taken along line 4—4 in FIG. 3
Figure 5:
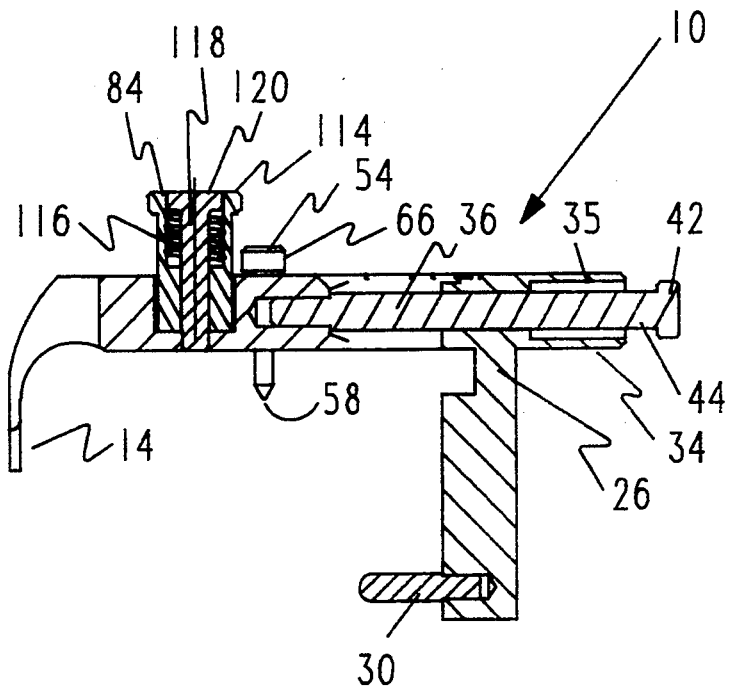
FIG. 5 is a through section of the jig taken along line 5—5 of FIG. 3.

Temporary pins 54, 56 are also provided to temporarily stabilize the jig 10. The pins 54, 56 have pointed ends 58, 60, an intermediate shaft 62, 64, and a head 66, 68. Bores 70, 72 through the plate 12 receive the pins 54, 56. The pins are secured within these bores by rings 74, 76 which are push fit onto the shafts 62, 64. As seen in FIG. 4, the bores have a relieved area 78, 80 so that the rings are received therein and the pins and rings can slide. The pointed ends of the pins can therefore be withdrawn in the base 12 and then pushed into the bone when the jig is in the desired position.

A transverse slot 82 in the plate 12 receives an adjustable drill guide, generally designated 84. The drill guide 84 permits the surgeon to accurately place guide bores to receive pegs on a femoral component of the knee prosthesis. These pegs are placed behind the condyles of the femoral component to be adjacent the femur. The placement of these bores and subsequent location of the condyle pins of the femoral component adjust the angular orientation of the femoral component about the axis of the femur. Such adjustments allow for variation in the anatomy of different patients.

The transverse slot 82 has a slight hour glass shape to accommodate angular adjustment of the drill guide 84. On outside walls 86, 88 a series of notches 92 permits indexed angular adjustment of the drill guide 84. The slot 82 also has a centrally located bore 94 for fastening drill guide 84 into the plate 12. Spaced radially outwardly from the central bore 94 are arcuate slots 96, 98 through which the surgeon will drill to make bores for the condyle pins.

The drill guide 84 has an elongated body 100 which fits in the slot 82. At opposite ends 102, 104 of the elongated body 100 there are through bores 106, 108 which guide a drill bit through the slots 96, 98 and into the distal end of the femur. Also at the end 104 is a tab 112 which selectively engages the notches 90 to orient the drill guide 84. In the center of the elongated body 100 is a housing 114 with a smaller through bore extending through the elongated body 100. A compression spring 116 is received within the housing 114. A guide pin 118, inserted through the compression spring 116, extending through the elongated body 100, and press fit into the central bore 94 in the body 12, holds the drill guide in the body or plate 12. A head 120 on the pin 118 captures the compression spring 116 within the housing 114. Radial openings 122 are provided around the housing 114 to permit access by sterilizing media, such as sterilizing gasses or steam. A rim 124 on the housing 114 provides a grip for the surgeon. In use, the surgeon would grasp the rim 124 and pull the drill guide 84 towards himself and away from the plate 12 thus disengaging the tab 112. The drill guide 84 can then be oriented angularly with respect to the axis of the femur. When the surgeon releases the drill guide 84, the tab 112 engages a selected one of the notches 90. We prefer providing the notches which permit the surgeon to select 0° (straight across the femoral condyles) or +3° or −3°. Of course, more selections could also be provided.

Those skilled in the art will recognize that our invention can be embodied in other specific forms without departing from the spirit or teachings thereof. The foregoing description, therefore, is to be considered to be in all respects illustrative and not restrictive, and the scope of our invention is to be defined by the following claims.

We claim as our invention:

1. A surgical jig for use by a surgeon when implanting a femoral component of a knee prosthesis, said jig comprising
   a plate adapted to be placed against a distal end of a femur of a patient,
   said plate having a transverse slot therein, said slot extending from a first end adapted to be adjacent a medial condyle of the femur to a second end adapted to be adjacent a lateral condyle of the femur when said plate is placed against said femur,
   a drill guide selectively received in said slot, said drill guide having a medial end and a lateral end, a bore for guiding a drill bit adjacent said medial end and a bore for guiding a drill bit adjacent said lateral end,
   spring means attaching said drill guide at a middle part of said drill guide to said plate at a middle part of said slot, said spring means permitting said drill guide to be partially withdrawn from said slot to change the orientation of said drill guide with respect to said plate, and
   means for retaining said drill guide in a selected position with respect to said plate.

2. The surgical jig according to claim 1 wherein said means for retaining further comprise interdigitating tabs and notches on at least one end of said drill guide and on said slot.

3. The surgical jig according to claim 2 wherein said tabs and notches comprise a tab on at least one end of said drill guide and a plurality of notches on at least one end of said slot.

4. The surgical jig according to claim 3 wherein said drill guide has a through bore at said middle part thereof and wherein said spring means comprise
   a spring,
   a guide pin having a head and a shaft, said shaft being inserted through said through bore and being attached to said middle part of said slot, and said spring being captured between said head and said drill guide, thereby pushing said drill guide into said slot.

5. The surgical jig according to claim 4 wherein said slot further comprises a pair of arcuate slots centered around said guide pin and under said bores in said medial and lateral ends of said drill guide.

6. The surgical jig according to claim 5 wherein said plate further comprises finger means for stabilizing said plate with respect to a proximal side of said distal end of said femur.

7. The surgical jig according to claim 6 further comprising at least one pin slidingly mounted in said plate, said pin being adapted to be pushed into said distal end of said femur to further stabilize said plate.

8. The surgical jig according to claim 7 further comprising gage means for measuring an anterior-posterior dimension of said distal end of said femur.

9. The surgical jig according to claim 8 further comprising width gauge means for measuring a medial-lateral dimension of said distal end of said femur.

* * * * *